(12) United States Patent
Rivier

(10) Patent No.: US 11,865,303 B2
(45) Date of Patent: Jan. 9, 2024

(54) PLASTIC FLANGE FOR A MEDICAL CONTAINER, MEDICAL CONTAINER INCLUDING THIS PLASTIC FLANGE, AND A METHOD FOR MANUFACTURING THIS MEDICAL CONTAINER

(71) Applicant: Becton Dickinson France, Le Pont de Claix (FR)

(72) Inventor: Cédric Rivier, Voreppe (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 17/623,051

(22) PCT Filed: Jun. 23, 2020

(86) PCT No.: PCT/EP2020/067527
§ 371 (c)(1),
(2) Date: Dec. 27, 2021

(87) PCT Pub. No.: WO2020/260297
PCT Pub. Date: Dec. 30, 2020

(65) Prior Publication Data
US 2022/0226572 A1 Jul. 21, 2022

(30) Foreign Application Priority Data
Jun. 28, 2019 (EP) ..................................... 19305879

(51) Int. Cl.
*A61M 5/178* (2006.01)
*A61M 5/32* (2006.01)
*G16H 20/17* (2018.01)

(52) U.S. Cl.
CPC ............ *A61M 5/178* (2013.01); *G16H 20/17* (2018.01); *A61M 2005/3247* (2013.01); *A61M 2205/60* (2013.01)

(58) Field of Classification Search
CPC ...... A61M 2005/3247; A61M 2205/60; A61M 5/3135; A61M 5/3137; A61M 2005/3131;
(Continued)

(56) References Cited

U.S. PATENT DOCUMENTS 1,798,116 A * 3/1931 Brockway ............. A61M 5/315
604/220
5,338,309 A * 8/1994 Imbert ................ A61M 5/3135
604/110
(Continued)

FOREIGN PATENT DOCUMENTS

WO 2008057150 A1 5/2008
WO 2014114938 A2 7/2014
(Continued)

*Primary Examiner* — James D Ponton
*Assistant Examiner* — Neeraja Gollamudi
(74) *Attorney, Agent, or Firm* — The Webb Law Firm

(57) ABSTRACT

A plastic flange for a medical container, the plastic flange defining an opening, the opening being surrounded by a peripheral collar, the collar providing a support to a user's fingers, wherein the flange comprises connecting means for connecting the flange to an external surface of a tubular barrel of the medical container, and wherein the flange further comprises a remotely readable electronic component for remote identification of the medical container, the remotely readable electronic component being embedded into the plastic flange.

13 Claims, 3 Drawing Sheets

(58) Field of Classification Search
CPC .. A61M 2205/6018; A61M 2205/6063; A61M 2205/6072; A61M 2205/6081; A61M 5/178; A61M 5/3129; A61J 2205/60
See application file for complete search history.

(56) References Cited

U.S. PATENT DOCUMENTS

| | | |
|---|---|---|
| 7,586,417 B2 | 9/2009 | Chisholm |
| 8,872,870 B2 | 10/2014 | Witzmann et al. |
| 9,387,292 B2 * | 7/2016 | Dowds ................ A61M 5/3202 |
| 9,501,734 B2 | 11/2016 | Morris |
| 2008/0149584 A1 | 6/2008 | Martinelli |
| 2009/0043253 A1 | 2/2009 | Podaima |
| 2010/0102967 A1 | 4/2010 | Lee et al. |
| 2011/0199187 A1 * | 8/2011 | Davidowitz ............ B01L 3/545 |
| | | 340/10.1 |
| 2016/0129193 A1 * | 5/2016 | Komann ............ A61M 5/31511 |
| | | 604/220 |

FOREIGN PATENT DOCUMENTS

| | | |
|---|---|---|
| WO | 2017070391 A2 | 4/2017 |
| WO | 2017157784 A1 | 9/2017 |

* cited by examiner

PLASTIC FLANGE FOR A MEDICAL CONTAINER, MEDICAL CONTAINER INCLUDING THIS PLASTIC FLANGE, AND A METHOD FOR MANUFACTURING THIS MEDICAL CONTAINER

CROSS-REFERENCE TO RELATED APPLICATIONS

This application is the United States national phase of International Application No. PCT/EP2020/067527 filed Jun. 23, 2020, and claims priority to European Patent Application No. 19305879.9 filed Jun. 28, 2019, the disclosures of which are hereby incorporated by reference in their entirety.

BACKGROUND OF THE INVENTION

Field of the Invention

The present invention relates to a plastic flange for a medical container, a medical container including this plastic flange, and a method for manufacturing this medical container.

Description of Related Art

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a medical container of the invention, and the "proximal direction" is to be understood as meaning the opposite direction to said direction of injection, that is to say the direction towards the user's hand holding a container as for an injection operation.

Injection devices, for example pre-fillable or prefilled syringes, usually comprise a hollow body or barrel forming a container for a medical product. This body comprises a distal end, usually provided with a needle, and a proximal end, provided with a flange allowing a user to place his or her fingers so as to exert a proximal pressure onto this flange.

There is an increasing need for individual traceability of the medical containers, such as injection devices, from the manufacturing process until at least the final use of said medical containers, typically the medical product injection.

It is known for example from document WO2017157784 a receptacle having a cylindrical lateral surface surrounded by a sequence of printed machine-readable unique identifier codes. These printed unique identifier codes allow tracking and tracing of each receptacle along a supply chain. However, these unique identifier codes are printed on an external side of the receptacle so that they may be removed or damaged for example during handling or use of the receptacle. Moreover, the unique identifier codes cover a portion of the receptacle so that they may have an impact on a customer visual inspection process.

It is further known from document U.S. Pat. No. 8,872,870 a method for glass-marking, wherein an array of readable marks may be formed by a laser on the external surface of a glass tube, for example for tracking purposes. However, the downsides of any laser marking methods are a possible damage to the glass material and an expensive manufacturing process. Besides, the laser-written array of mark requires having a visual access to the glass tube so as to be read, so that the reading operation cannot occur at any time. The laser-written array of mark may further have an impact on a customer visual inspection process.

It is further known from document WO2014114938A2 an RFID tag for location inside a tubular base portion of a freestanding cryogenic vial. The document US2011199187A1 discloses an RFID tag inserted into a recess at the bottom of a vial. The document US2010102967A1 discloses a container lid with a removable RFID tag. It is known from document US2008149584A1 a product packaging that comprises a cap on a transparent bottle, where the cap includes an RFID chip and antenna. The document WO2008057150A1 further discloses a container that includes an RFID insert having a disable feature.

In this context, an object of the present invention is to provide a plastic flange that alleviates the above-mentioned drawbacks by allowing easy individual identification of a medical container from the first step of the manufacturing step to the final use, typically the injection, or disposal step, with no impact on visual inspection and with few or no risks of being removed or damaged.

SUMMARY OF THE INVENTION

An aspect of the invention is a plastic flange for a medical container, said plastic flange defining an opening, said opening being surrounded by a peripheral collar, said collar providing a support to a user's fingers, wherein the flange comprises connecting means for connecting said flange to an external surface of a tubular barrel of the medical container, and wherein the flange further comprises a remotely readable electronic component for remote identification of the medical container, said remotely readable electronic component being at least partially embedded into the plastic flange.

By electronic component embedded in the plastic flange it should be understood that the plastic flange fully or at least partially encases the electronic component, so that the electronic component is protected from the external environment and therefore cannot be damaged or removed.

By remotely readable electronic component for identification of the medical container it is meant that the electronic component comprises electronically stored information that may be remotely read by a reading machine, such as a RFID reader, enabling identification of the medical container to which the flange of the invention is intended to be assembled.

The plastic flange of the invention thus allows having an individual traceability of each medical container from the manufacturing step to the final use of the medical container or to the disposal of said medical container. Besides, because the electronic component is at least partially encased in the plastic flange, it is protected from removal or external damage that may occur due to the packaging, sterilization, storing, distribution or the use of the medical container. Furthermore, the electronic component being located inside the flange, there is no impact on customer visual inspection process. It is also contemplated that the electronic component permits remote and therefore easy identification of the medical container. The electronic component does not require a direct visual perspective from a reading machine so that the reading may occur at any time without a need to unpackage the medical container. Moreover, the electronic component is integrated inside the flange so that there is advantageously no additional thickness to the medical container barrel, and thus no change is required regarding the packaging or storing of the medical container. Due to the connecting means, the flange of the invention may be advantageously mounted on a glass medical container so that the flange of the invention allows reliable and easy identification of a glass medical container without the drawbacks of the state of the art.

In a preferred embodiment, the remotely readable electronic component is selected from the group consisting of a RFID tag, a ultra wide-band real-time location system (RTLS), a wifi RTLS and an infrared RTLS. Advantageously, the remotely readable electronic component is a RFID tag including a RFID chip and a RFID antenna. Preferably, the RFID antenna extends around the opening.

Preferably, the plastic flange is connected to the tubular barrel by glueing, screwing or fitting.

Preferably, the connecting means comprise a plurality of bumps radially protruding from an inner lateral wall of the flange and configured to abut against the external surface of the tubular barrel.

This permits to maintain the flange perpendicular to the tubular barrel.

Preferably, the plurality of bumps comprises proximal blocking surfaces configured to abut against a bead of the tubular barrel.

This allows preventing movement of the barrel from the flange in a distal direction when the medical device is used for injection of a medical or pharmaceutical composition and thus maintain the barrel secured to the flange.

Preferably, the connecting means comprise a distal shoulder configured to receive a proximal end of the tubular barrel and arranged opposite the proximal blocking surfaces.

Thus, the tubular barrel is axially blocked relative to the flange.

Preferably, adjacent bumps of said plurality of bumps define an axial channel configured to be filled with a glue material.

This permits the addition of a glue material between the flange and the tubular barrel in order to prevent any rotational movement of the flange relative to the barrel.

Preferably, the connecting means comprise at least one circular channel configured to establish a fluid connection between adjacent axial channels.

This permits the glue material to flow in all filling rooms at once in order to perform the glue distribution in a single operation.

The circular channel may extend between the distal shoulder and the plurality of bumps.

The RFID tag may advantageously be overmolded in the plastic flange.

Preferably, the remotely readable electronic component is totally overmolded in the plastic flange. Alternatively, the remotely readable electronic component is embedded between the plastic flange and the glue material.

This results in no change in the flange dimensions with regard to standard flange dimensions so as to avoid investment costs.

The RFID tag may be molded in a two-shot injection molding process. More particularly, the RFID tag is positioned as an insert into the mold. A first part of the flange is formed by a first injection of a plastic material and partially covers the RFID tag. A second part of the flange, that totally encapuslates the RFID tag together with the first part, is then formed by a second injection step of a plastic material that may be the same plastic material as the first part or a different plastic material.

The RFID tag may be substantially arranged at the middle of the plastic flange.

Another aspect of the invention is a medical container comprising:
a tubular barrel for receiving a medical product,
a plastic flange as above described, said plastic flange protruding from an external surface of said barrel so as to provide a user's fingers support.

Preferably, the tubular barrel is made of a glass material.

Another aspect of the invention is a method for manufacturing a medical container as above-described, said method comprising the steps of:
providing a plastic flange as above-described,
providing the tubular barrel,
connecting the plastic to the tubular barrel by means of the flange connecting means.

Preferably, the method comprises at least one step chosen among the following steps:
distributing a glue material between the flange and the tubular barrel;
screwing the flange onto the external surface of the tubular barrel; or
snap fitting the flange onto the external surface of the tubural barrel.

BRIEF DESCRIPTION OF THE DRAWING

The invention and the advantages arising therefrom will clearly emerge from the detailed description that is given below with reference to the appended drawings as follows.

DETAILED DESCRIPTION

Figure 1:
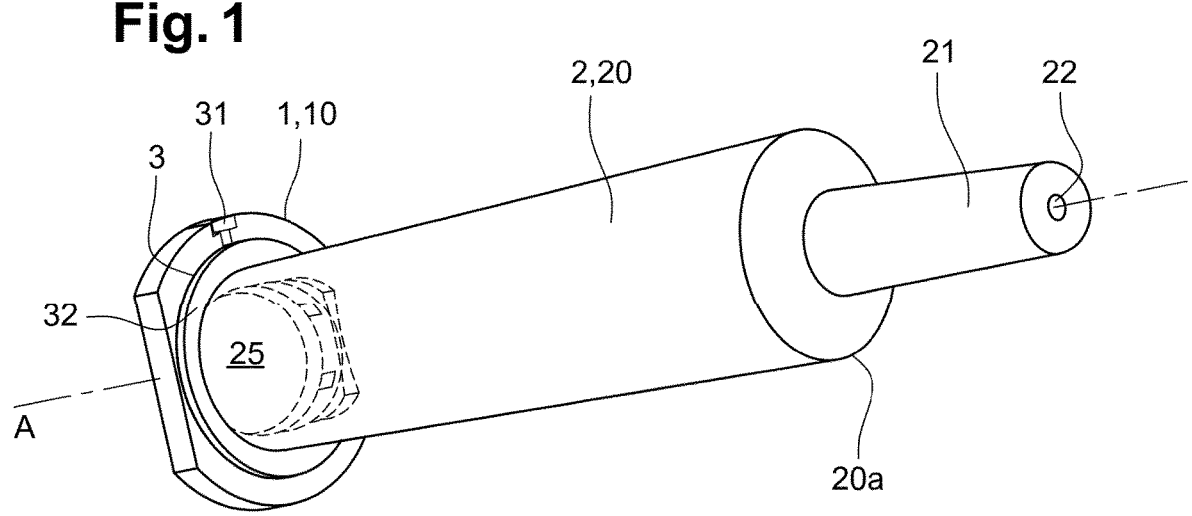
FIG. 1 is a perspective view of a medical container having a flange according to the invention.
Figure 2:
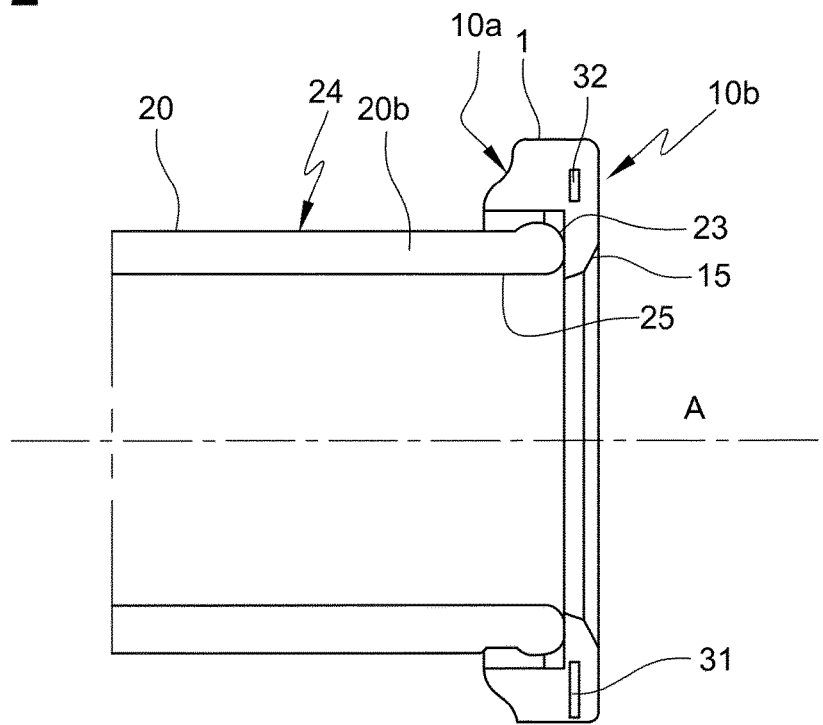
FIG. 2 is a side section view of a flange according to the invention receiving the barrel of a medical container.
Figure 3:
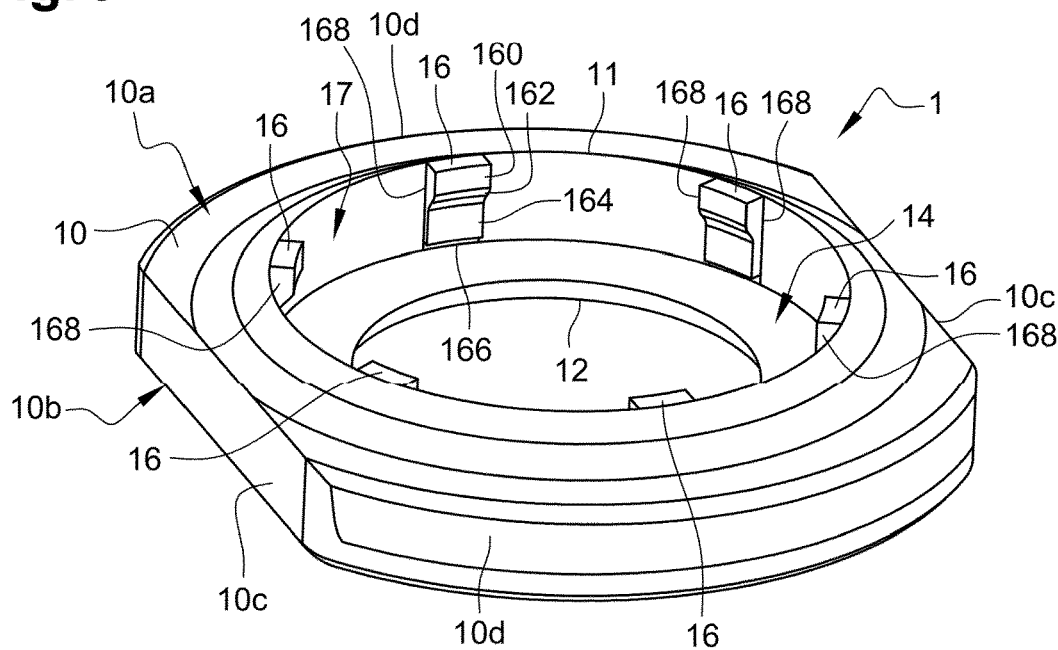
FIG. 3 is a perspective view of a flange according to the invention.

With reference to FIGS. 1, 2 and 3 is shown a plastic flange 1 according to the invention. As visible on FIGS. 1 and 2, the plastic flange 1 is designed to be mounted on a medical container 2, such as a syringe. The medical container 2 may comprise a tubular barrel 20 that defines a reservoir for containing a medical product. As shown on FIG. 1, the tubular barrel 20 may have a distal end 20a including a preferably tapered distal tip 21 defining an axial passageway 22 in fluid communication with the reservoir. The distal tip 21 may allow mounting of an adaptor or a needle thereof. As shown on FIG. 2, the tubular barrel 20 includes a proximal end 20b that defines an aperture 25 for receiving a plunger rod (not shown). Said proximal end 20b may present a circular bead 23 that protrudes from an external lateral surface 24 of said tubular barrel 20. It should be noted that the flange 1 is made of a plastic material, preferably a hard plastic material such as polycarbonate, polypropylene or cyclic olefin copolymer (COC), while the medical container 2 may be made of a glass material. In an embodiment not shown, the flange 1 may comprise two or more different plastic materials.

With reference for example to FIG. 1, the plastic flange 1 comprises a remotely readable electronic component 3 for remote identification of the medical container 2 by means of a remote reading machine. Advantageously, the remotely readable electronic component 3 is a RFID tag for identification of the medical container 2, preferably a passive RFID tag. The RFID tag may be a passive RFID tag. The RFID tag may be read by a RFID reader, without requiring a direct perspective view on the plastic flange 1. The RFID tag is located within the collar 10 of the plastic flange 1. The RFID tag may be substantially arranged at the middle of the plastic flange 1 width. The RFID tag includes a RFID chip 31 and a RFID antenna 32. The RFID chip 31 may at least include a storage unit that stores a unique device identification (UDI), allowing the identification of the medical device. The RFID antenna 32 may extend all around an opening 11 of the plastic flange 10, as visible on FIG. 1.

The RFID tag may be partially or completely embedded into the plastic flange 1, so as to be protected from the outside environment. When assembled to the medical container 2, the plastic flange 1 preferably completely encases the RFID tag. For example, the RFID tag may be either totally encased in the sole collar 10 of the plastic flange 1 or totally encased by the collar 10 plus a glue material 30 that fixes the plastic flange 1 to the tubular barrel 20.

The RFID tag may advantageously be overmolded within the plastic flange 1.

For example, the RFID tag is molded in a two-shot injection molding process. More particularly, the RFID tag is positioned as an insert into the mold. A first part of the flange is formed by a first injection of a plastic material. A second part of the flange, that encapuslates the RFID tag together with the first part, is then formed by a second injection step of a plastic material that may be the same plastic material as the first part or a different plastic material.

Preferably, the RFID tag is totally overmolded in the plastic flange 1. Alternatively, the RFID tag is partially overmolded in the plastic flange 1 (for example, a portion of the RFID tag may be flush with a surface of the plastic material of the flange 1) and then completely embedded into the plastic flange 1 by addition of the glue material 30 that fully covers the RFID tag, the glue material 30 thus directly being in contact with the RFID tag.

As shown on FIG. 3, the plastic flange 1 comprises a collar 10 that defines the central opening 11. The collar 10 has a proximal face 10b and an opposite distal face 10a, as visible on FIG. 2. Said distal face 10a is designed to provide a support to a user's fingers when the medical container 2 is being used for example for an injection operation. The collar 10 may have a peripheral rim formed by two parallel edges 10c connected by two curved edges 10d. In another embodiment (not shown), the peripheral rim may be totally circular. The opening 11 is configured to allow insertion of the tubular barrel 20 of the medical container 2 as will be hereinafter described in further detail. As shown on FIG. 2, the opening 11 may be centered around a longitudinal axis A of the medical container 2.

The plastic flange 1 may further define a through-aperture 12 that is configured to be superimposed to the aperture 25 of the tubular barrel 20 so as to allow passage of a plunger rod into the reservoir. The through-aperture 12 and the opening 11 of the flange may be coaxial. The through-aperture 12 may be centered around the longitudinal axis A of the medical container 2. As shown on FIG. 3, the through-aperture 12 may have a lower diameter than the opening 11 of the flange 1, thereby defining a distal shoulder 14 that separates the opening 11 and the through-aperture 12 of the flange 1. The through-aperture 12 is proximally located relative to the opening 11 of the flange. The plastic flange 1 may present a proximal bevelled edge 15 that may be provided on the proximal face 10b of the collar and that surrounds the through-aperture 12, as visible for example on FIG. 2.

The flange 1 comprises connecting means, said connecting means being configured to connect the flange 1 to an external surface of the tubular barrel 20 of the medical container 2. The connecting means are preferably located inside the opening 11 of the flange 1.

As shown on FIG. 3, the connecting means may comprise a plurality of bumps 16 radially protruding from an inner lateral wall 17 of the flange 1. The inner lateral surface 17 may delimit the opening 11. The bumps 16 are configured to abut against the external lateral surface 24 of the tubular barrel 20, as illustrated for example on FIG. 4. The bumps 16 may be regularly angularly distributed around the longitudinal axis A and preferably inside the opening 11. The connecting means comprise at least one, preferably two bumps 16. In the illustrated embodiment, the connecting means comprise six bumps 16. They may otherwise comprise three, four, five or more, bumps 16.

Figure 5:
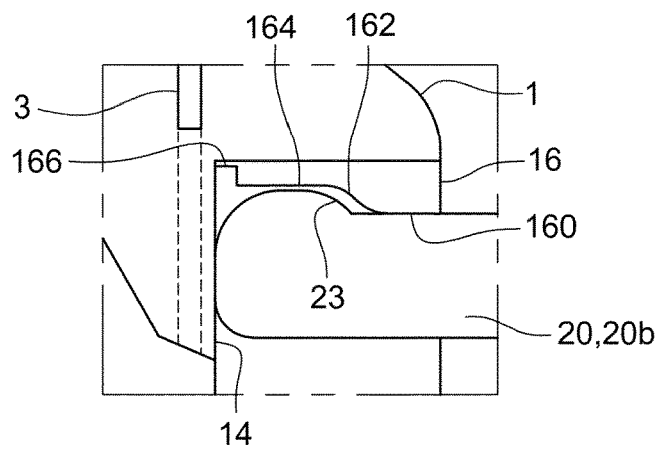
FIG. 5 is a partial side section view of a flange according to the invention receiving the barrel of a medical container.

As shown on FIG. 5, the bumps 16 may include a radial abutment surface 160 that is configured to abut against the external surface 24 of the tubular barrel 20. The diameter that define said radial abutment surface 160 may be lower than the external diameter of the tubular barrel 20 so that the bumps 16 are configured to exert a radial pressure against the external surface 24 of the tubular barrel 20. To that end, the flange or the bumps 16 may be made of a resilient material. The radial abutment surfaces 160 may be flat or may preferably have a shape that is complementary to the shape of the external lateral surface 24 of the tubular barrel 20, such as a cylindrical shape.

Still with reference to FIG. 5, the bumps 16 may comprise a proximal blocking surface 162 that is configured to block a distal movement of the tubular barrel 20 relative to the flange. For example, the blocking surfaces 162 abut against the bead 23 provided at the proximal end of the end. As visible on FIG. 5, the proximal blocking surfaces 162 may be slanted relative to a longitudinal axis A of the medical container 2. The proximal blocking surfaces 162 are proximally arranged relative to the first radial abutment surfaces 160.

The bumps 16 may define a radial recess 164 configured to receive a corresponding protruding portion of the tubular barrel 20, such as the bead 23 of said tubular barrel 20. The recesses 164 have a bottom abutment surface that may be configured to abut against the tubular barrel 20 so as to limit a pivot movement of the tubular barrel 20 relative to the flange 1 around an axis that is orthogonal to the longitudinal axis A. The bottom abutment surfaces may define a diameter that is greater than that defined by the above-described radial abutment surfaces 160. The recesses 164 may have a shape that is complementary to a shape of the external lateral surface 24 of the tubular barrel 20. The recesses 164 and their bottom abutment surfaces are proximally located relative to the proximal blocking surfaces 162.

As shown on FIG. 5, the proximal end 20b of the tubular barrel 20 abuts against the distal shoulder 14 so that the distal shoulder 14 blocks a proximal movement of the tubular barrel 20 relative to the flange 1. The distal shoulder 14 may be flat and preferably orthogonal to the longitudinal axis A. The distal shoulder 14 faces the proximal blocking surfaces 162 of the bumps 16.

Figure 4:
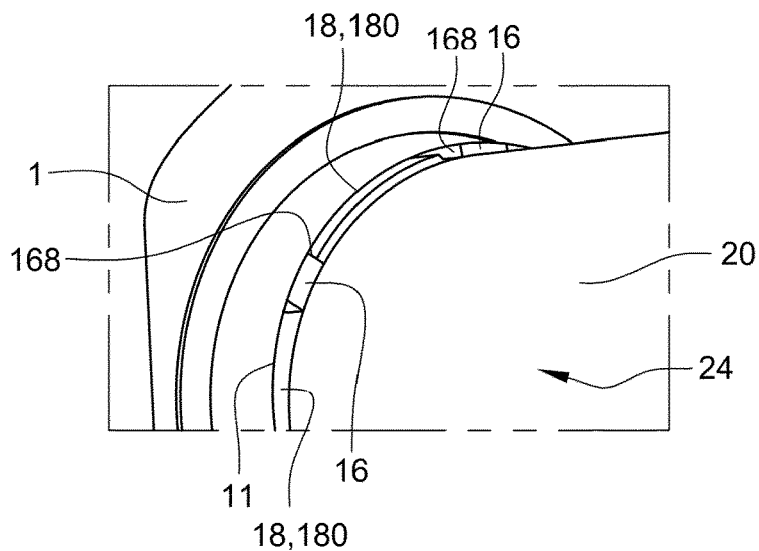
FIG. 4 is a partial perspective view of a flange according to the invention receiving the barrel of a medical container.
Figure 6:
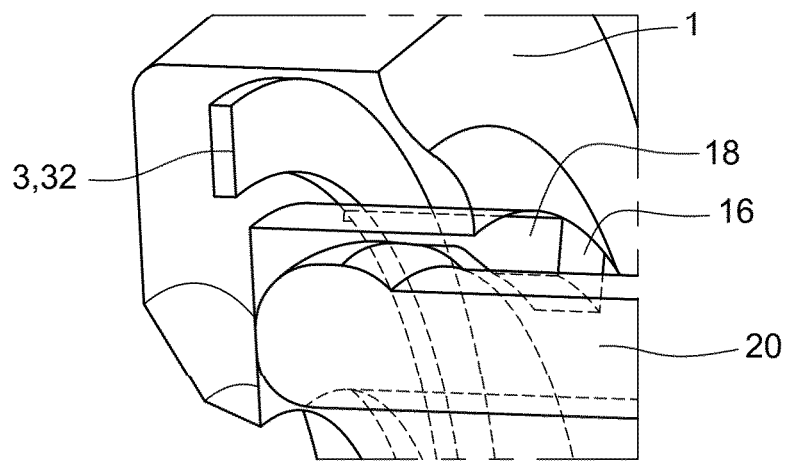
FIG. 6 is a partial perspective section view of a flange according to the invention receiving the barrel of a medical container.
Figure 7:
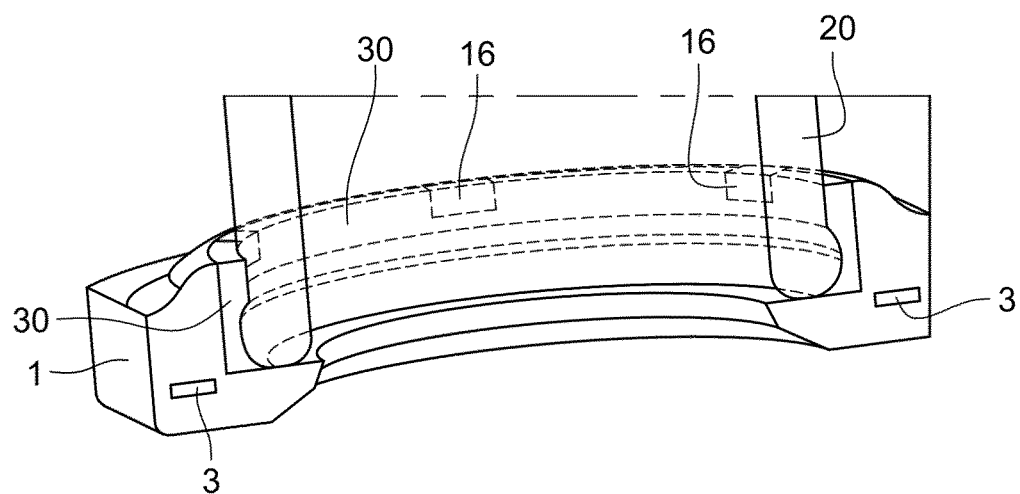
FIG. 7 is a partial perspective section view of a medical container having a flange according to the invention.

As illustrated on FIG. 4 or 6, adjacent bumps 16 may define therebetween an axial channel 18 that is configured to be filled with the glue material 30. At least one of the axial channels 18 may have a distal open end 180 allowing entry of said glue material 30. The axial channels 18 may longitudinally extend along the longitudinal axis A and laterally extend around said longitudinal axis A. The axial channel 18 may have a cylindrical shape. The axial channel 18 is indeed delimited by lateral walls 168 of the bumps 16, the inner lateral surface 17 of the flange 1, and the external surface 24 of the tubular barrel 20.

Figure 8:
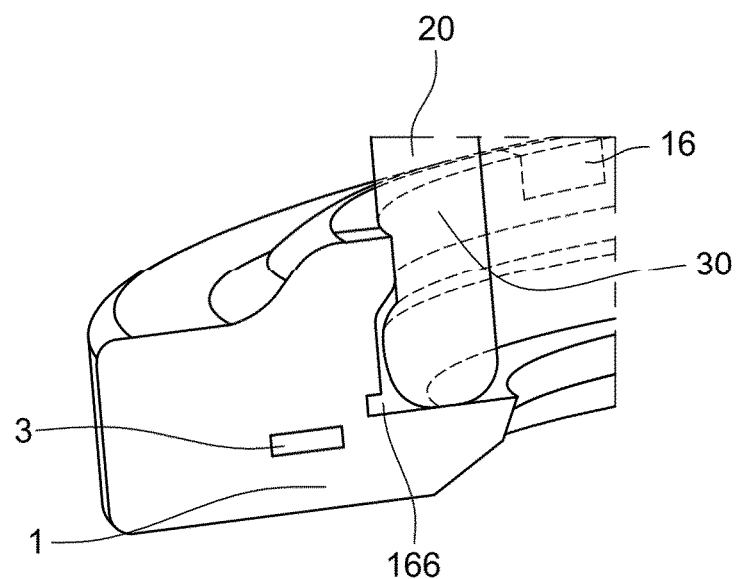
FIG. 8 is a partial side section view of a medical container having a flange according to the invention.

The glue material 30 may be chosen between a hol-melt adhesive and glue, for example glue with an acrylate base As shown on FIGS. 3, 5 and 8, the connecting means may further comprise at least one circular channel 166 establishing a fluid communication between at least two adjacent axial channels 18. The circular channels 166 may interconnect the axial channels 18 all together so as to allow the glue material 30 to flow in all spaces located between the external surface 24 of the tubular barrel 20 and the flange 1. The circular channel 166 may be formed by a groove arranged between the distal shoulder 14 and the bumps 16, and may be proximally located relative to the recesses 164 of said bumps 16. For example, the circular channel 166 is a groove defined in the bumps 16 or in the distal shoulder 14 or in the inner lateral surface 17 of the flange 1.

It should be noted that the connecting means may alternatively comprise snap-fit, press-fit or thread elements in order to position or secure the flange to the tubular barrel 20. The plastic flange 1 may thus be connected to the tubular barrel 20 by gluing, screwing or fitting.

The invention also relates to the medical container 2 comprising the tubular barrel 20 for receiving a medical product, and the above-described plastic flange 1 protruding from an external lateral surface of said tubular barrel 20, wherein the tubular barrel 20 is made of a glass material, the tubular barrel 20 and the plastic flange 1 being secured together by the connecting means.

The invention also relates to a method for manufacturing said medical container 2, wherein the method comprises the steps of providing a plastic flange 1 as above-described which comprises the remotely readable electronic component 3, providing the tubular barrel 20, and connecting the plastic flange 1 to the tubular barrel 20 by means of the flange connecting means.

The step of providing the plastic flange 1 may include overmolding the remotely readable electronic component 3, for example during a two-shot injection molding process.

The step of connecting the plastic flange 1 to the tubular barrel 20 may include distributing a glue material 30 between the flange 1 and the tubular barrel 20, or screwing the flange 1 onto the external lateral surface 24 of the tubular barrel 20, or snap fitting the flange 1 onto the external lateral surface 24 of the tubural barrel 20.

The invention claimed is:

1. A plastic flange for a syringe with a tubular barrel, comprising:
   an opening being defined by the plastic flange;
   a peripheral collar surrounding the opening, said peripheral collar providing a support to a user's fingers;
   a through-aperture configured to allow passage of a plunger rod into a reservoir defined by the tubular barrel of the syringe, said plastic flange adapted for connection to an external surface of the tubular barrel of the syringe through the opening of the plastic flange;
   a plurality of bumps radially protruding from an inner lateral wall of the plastic flange and configured to abut against the external surface of the tubular barrel, wherein adjacent bumps of said plurality of bumps define an axial channel configured to be filled with a glue material, and wherein the plastic flange comprises at least one circular channel configured to establish a fluid connection between adjacent axial channels; and
   a remotely readable electronic component for remote identification of the syringe, said remotely readable electronic component being at least partially embedded into the plastic flange.

2. The plastic flange according to claim 1, wherein the remotely readable electronic component is a RFID tag including a RFID chip and a RFID antenna, said RFID antenna extending around the opening.

3. The plastic flange according to claim 1, wherein the plastic flange is connected to the tubular barrel by gluing, screwing or fitting.

4. The plastic flange according to claim 1, wherein the plurality of bumps comprises proximal blocking surfaces configured to abut against a bead of the tubular barrel.

5. The plastic flange according to claim 4, wherein the plastic flange comprises a distal shoulder configured to receive a proximal end of the tubular barrel and arranged opposite the proximal blocking surfaces.

6. The plastic flange according to claim 1, wherein the remotely readable electronic component is totally overmolded in the plastic flange.

7. A syringe comprising:
   a tubular barrel for receiving a medical product; and
   a plastic flange according to claim 1, said plastic flange protruding from an external surface of said tubular barrel so as to provide a user's fingers support.

8. The syringe according to claim 7, wherein the tubular barrel is made of a glass material.

9. A method for manufacturing a syringe, said method comprising the steps of:
   providing the plastic flange of claim 1;
   providing the tubular barrel; and
   connecting the plastic flange to the tubular barrel, wherein the plastic flange is adapted for connection to an external surface of the tubular barrel of the syringe through the opening of the plastic flange.

10. The method according to claim 9 further comprising:
    distributing a glue material between the plastic flange and the tubular barrel.

11. The method according to claim 9 further comprising:
    screwing the plastic flange onto the external surface of the tubular barrel.

12. The method according to claim 9 further comprising:
    snap fitting the plastic flange onto the external surface of the tubular barrel.

13. A plastic flange for a syringe with a tubular barrel, comprising:
    an opening being defined by the plastic flange;
    a peripheral collar surrounding the opening, said peripheral collar providing a support to a user's fingers;
    a through-aperture configured to allow passage of a plunger rod into a reservoir defined by the tubular barrel of the syringe, said plastic flange adapted for connection to an external surface of the tubular barrel of the syringe through the opening of the plastic flange;
    a plurality of bumps radially protruding from an inner lateral wall of the plastic flange and configured to abut against the external surface of the tubular barrel, wherein adjacent bumps of said plurality of bumps define an axial channel configured to be filled with a glue material; and
a remotely readable electronic component for remote identification of the syringe, said remotely readable electronic component being at least partially embedded into the plastic flange, wherein the remotely readable electronic component is embedded between the plastic flange and the glue material.

\* \* \* \* \*